United States Patent

Leconte et al.

Patent Number: 5,117,036
Date of Patent: May 26, 1992

[54] PREPARATION OF AROMATIC CARBAMATES

[75] Inventors: Philippe Leconte, Mulhouse; Francois Metz, Lyons, both of France

[73] Assignee: Rhone-Poulenc Chimie, Courbevoie, France

[21] Appl. No.: 313,864

[22] Filed: Feb. 23, 1989

[30] Foreign Application Priority Data

Feb. 23, 1988 [FR] France .................. 88 02440

[51] Int. Cl.$^5$ ............................................ C07C 261/00
[52] U.S. Cl. ........................................ 560/24; 560/25; 560/26
[58] Field of Search ............................... 560/24, 25, 26

[56] References Cited

U.S. PATENT DOCUMENTS

3,454,620  7/1969  Gamlen .................. 560/25

FOREIGN PATENT DOCUMENTS

0086281  8/1983  European Pat. Off.
0169650  1/1986  European Pat. Off.
0231045  8/1987  European Pat. Off.

*Primary Examiner*—Bruce Gray
*Attorney, Agent, or Firm*—Burns, Doane, Swecker & Mathis

[57] ABSTRACT

Aromatic carbamates are selectively and actively prepared by reacting (a) at least one nitroaromatic compound with (b) carbon monoxide and (c) at least one organic compound bearing at least one hydroxyl group, in the presence of:

(d) a palladium-based catalyst,
(e) at least one coordinate of the formula:

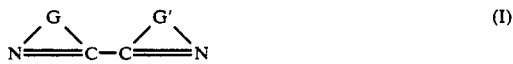

in which each of G and G', which may be identical or different, is a bridging group which contains 3 or 4 atoms, at least 2 of which are carbon atoms, with the proviso that G and G' may be linked to each other, and (f) at least one protonic acid in which no proton is linked to a halogen atom, and wherein the amount of palladium present in the reaction medium is less than or equal to 0.01 mole per liter of such reaction medium and the reaction is carried out such that:

(i) either the molar ratio (H$^+$/Pd) is higher than 150, and/or
(ii) the molar ratio (coordinate/Pd) is higher than 20.

16 Claims, No Drawings

PREPARATION OF AROMATIC CARBAMATES

BACKGROUND OF THE INVENTION

1. Field of the Invention

The present invention relates to the preparation of aromatic carbamates by reacting at least one nitroaromatic compound, carbon monoxide and at least one organic compound bearing at least one hydroxyl group in the presence of a palladium-based catalyst.

2. Description of the Prior Art

The carbamates under consideration (or urethanes) are precursors of isocyanates, and the isocyanates are currently widely used, for example in the production of polyurethanes. Among the most important isocyanates, very particular mention will be made of diisocyanatotoluene (TDI) and methylenediphenyl diisocyanate (MDI), which hitherto have been produced industrially by phosgenation of the corresponding diamines. They frequently are in the form of mixtures of isomers.

Various processes have already been proposed to this art for reducing nitroaromatic compounds using carbon monoxide and a lower alkanol in the presence of various catalyst systems; all of which exhibit at least one of the following major disadvantages:

(1) presence of undesirable metal impurities in the reaction product;

(2) high risk of corrosion of the apparatus due to the chloride ions originating, in most cases, from the ferrous or ferric chlorides employed as cocatalysts in the reaction.

More recently, a process has been proposed to the art for preparing aromatic carbamates by reacting (i) at least one nitroaromatic compound, (ii) carbon monoxide and (iii) at least one organic compound bearing at least one hydroxyl group in the presence of a palladium-based catalyst. In fact, such a process is described in European Patent Application EP-A-0,086,281, the distinguishing characteristic of which process comprising using particular classes of coordinates, typical representatives of which being tetraphenyldiphosphinoethane, 2,2'-dipyridyl and 1,10-phenanthroline, and which are used in practice in a proportion of 0.02 to 20 moles per gram-atom of palladium present in the reaction medium. In this same application, it is also proposed to carry out the reaction in question in the presence of an acid in order to increase the reaction rate and, if appropriate, the selectivity for the required carbamate. These acids are actually employed in a proportion of 0.01 to 150 equivalents per gram-atom of palladium present in the reaction medium.

However, while the principal advantage of a process of this type is not in dispute, its development on an industrial scale is inhibited by the relatively large amounts of palladium or of palladium compounds which have to be used in the reaction, in order to obtain an appropriate activity of the catalyst system and a acceptable product selectivity.

Notwithstanding the cost of the metallic catalyst, which necessitates the recycling thereof, and the versatile nature of said metal or its compounds, having to use large amounts of a metal of this type, or compounds thereof, makes it difficult to recycle it or them and increase the risk that the metal will be deposited, particularly on the walls of the equipment. Serious need therefor exists to carry out the reaction in question using restricted amounts of palladium or of palladium compounds. However, when such amounts are limited in order to attain at most a concentration on the order of 0.01 mole per liter, expressed in moles of palladium per liter of reaction medium, both a prohibitive decrease in the selectivity for the desired reaction product and a marked decrease in activity are realized.

SUMMARY OF THE INVENTION

Accordingly, a major object of the present invention is the provision of an improved process for the palladium-catalyzed production of aromatic carbamates, which improved process requires lesser amounts of catalyst and conspicuously avoids those disadvantages and drawbacks to data characterizing the state of this art.

Briefly, the present invention features a process for the preparation of aromatic carbamates by reacting (a) at least one nitroaromatic compound, (b) carbon monoxide and (c) at least one organic compound bearing at least one hydroxyl group, in the presence of (d) a palladium based catalyst, (e) at least one coordinate of the formula:

in which each of G and G', which may be identical or different, is a bridging group which contains 3 or 4 atoms at least 2 of which are carbon atoms, with the proviso that G and G' may be linked to each other, and (f) at least one protonic acid in which no proton is linked to a halogen atom, characterized in that the amount of palladium present in the reaction medium is less than or equal to 0.01 mole per liter of said medium and in that the reaction is carried out such that:

(i) either the molar ratio (H+/Pd) is higher than 150, and/or (ii) the molar ratio (coordinate/Pd) is higher than 20.

DETAILED DESCRIPTION OF THE PREFERRED EMBODIMENTS OF THE INVENTION

More particularly according to the present invention, by "at least one nitroaromatic compound" is intended at least one compound containing at least one $NO_2$ group directly bonded to a carbon atom which is an aromatic ring carbon atom. Among the nitroaromatic compounds which are suitable starting materials in the process of the invention are nitrobenzene and its homologs obtained by substitution of one or more hydrogen atoms by one or more alkyl, alkoxy, aryl or aryloxy groups; dinitrobenzenes and their homologs obtained by substitution of one or more hydrogen atoms by one or more alkyl, alkoxy, aryl or aryloxy groups; and the polynitrobenzenes. Nitrotoluenes, dinitrotoluenes and 4,4'-dinitrodiphenylmethane are especially representative. Obviously, mixtures of two or more nitroaromatic compounds may be employed and, in particular, mixtures of the 2,4- and 2,6-isomers of dinitrotoluene.

The at least one nitroaromatic compound is reacted with carbon monoxide and at least one organic compound bearing at least one hydroxyl group, such hydroxylated compounds advantageously having the following general formula (II):

in which n is an integer other than zero and not exceeding 4, and $R^1$ is an alkyl or aralkyl radical which may be substituted by one or more halogen atoms and/or alkoxy groups containing not more than 4 carbon atoms, and which contains not more than 20 carbon atoms and, preferably, not more than 6 carbon atoms.

Exemplary of the monohydroxylated compounds corresponding to the general formula (II), representative are methanol, ethanol, n-propanol and secondary propanol, 1-hexanol, 1-dodecanol, 1-hexadecanol, chlorobenzyl alcohol, methoxybenzyl alcohol, butoxyethanol, cyclohexanol and trifluoroethanol.

Exemplary of the polyhydroxylated compounds corresponding to the general formula (II), representative are ethylene glycol, diethylene glycol, propylene glycol, glycerol and trimethylolpropane.

Mixtures of two or more compounds may obviously be used.

Methanol, ethanol, propanol, isopropanol and ethylene glycol are more particularly suitable according to the invention; the alkanols containing not more than 4 carbon atoms are advantageously used.

The relationship between the amounts of the nitroaromatic compound and the hydroxylated organic compound is not critical; either may be employed in excess. In practice, it has been determined to be advantageous to conduct the reaction using an excess of the hydroxylated organic compound, which then serves as a reaction solvent. It is also possible to conduct the reaction in an inert diluent such as an optionally halogenated aliphatic or aromatic hydrocarbon, and especially benzene, toluene, chlorobenzene or hexane.

The process according to the invention requires the presence of palladium or of palladium compounds.

Any source of palladium may be employed according to this invention. In fact, it is possible to use metallic palladium, either alone or deposited on an inert support such as carbon black or alumina, or to use palladium salts or complexes.

Most of these sources of palladium will be soluble in the reaction medium under the conditions of the reaction in question. By way of specific examples of palladium compounds which are suitable for use in the present invention, the following are representative:

(i) palladium carboxylates in which the anion preferably contains not more than 12 carbon atoms and, in particular, palladium acetate and palladium propionate;

(ii) palladium halides and, in particular, palladium chloride and palladium bromide;

(iii) palladium acetylacetonate, and complexes of palladium and of dibenzylideneacetone such as $Pd(dba)_3$.

Palladium acetate is particularly suitable according to this invention.

As hereinbefore indicated, the concentration of palladium in the reaction medium is less than 0.01 mole per liter. This concentration is advantageously less than 0.0025 mole per liter. This concentration is generally at least equal to $10^{-4}$ mole/liter, in order to effect an appreciable conversion of the nitroaromatic compound(s).

The process according to the present invention also requires the presence, in the reaction medium, of at least one coordinate of the above formula (I), in which G and G' are also defined, i.e.:

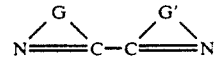

When the bridging group(s) G and/or G' contains (contain) one (or two) atom(s) other than carbon atoms, these atoms are preferably nitrogen atoms, G and G' may additionally be linked to each other by a group of two carbon atoms to form a coordinate of formula (I) exhibiting the 1,10-phenanthroline skeleton.

Exemplary of the coordinates of general formula (I), representative are 2,2'-dipyridyl, 4,4'-dimethyl-2,2'-dipyridyl, 4,4'-dimethoxy-2,2'-dipyridyl, 4,4'-dicarboxy- 2,2'-dipyridyl, 4,4'-dichloro-2,2'-dipyridyl, 2,2'-diquinolyl, 1,10-phenanthroline, 4,7-diphenyl-1,10-phenanthroline, 3,4,7,8-tetramethyl-1,10-phenanthroline and 4,7-dimethyl-1,10-phenanthroline.

1,10-Phenanthroline and its derivatives which are not substituted in the positions 2 and/or 9 are more particularly suitable as coordinates according to the present invention.

1,10-Phenanthroline is preferably used.

The amount of coordinate to be used may vary over wide limits when, furthermore, the amount of protonic acid which is used is such that the molar ratio $H^+/Pd$ is higher than 150. In general, the amount of coordinate is at least one mole per mole of palladium. It is advantageously higher than 20 moles per mole of palladium. No advantage is noted when the molar ratio (coordinate/palladium) exceeds 2,000. This molar ratio preferably ranges from 100 to 1,500.

The process according to the invention additionally requires the presence of a protonic acid in which no proton is linked to a halogen atom. Many categories of protonic acids are suitable and the following are exemplary:

(i) $HBF_4$, $HPF_6$, $H_2SiF_6$ and, more generally, the acids formed, in situ if appropriate, by reaction of HF with a Lewis acid, such as $BF_3$ and $PF_5$;

(ii) $HClO_4$;

(iii) sulfonic acids and, in particular, 2,4,6-trimethylbenzenesulfonic acid;

(iv) carboxylic acids such as acetic acid, mesitylenecarboxylic acid and trifluoroacetic acid.

A protonic acid having a pK, higher than 2, which is not esterifiable, or difficult to esterify under the particular reaction conditions, is preferably used. Mesitylenecarboxylic acid is particularly suitable for carrying out the subject process.

The amount of protonic acid to be employed according to the present invention may vary over very wide limits when, furthermore, the amount of coordinate, as defined above, which is used is such that the molar ratio (coordinate/Pd) is higher than 20. In general, the amount of protonic acid is at least 0.01 mole per mole of palladium. No advantage is observed when said molar ratio exceeds 5,000. To satisfactorily carry out the process of the present invention, the molar ratio $H^+/Pd$ is higher than 150. Such molar ratio preferably ranges from 200 to 2,500.

Also as above indicated, according to this invention it is essential that at least one of the two following conditions, relating to molar ratios, be observed:

(i) $H^+/Pd > 150$ (ii) coordinate/Pd > 20

Both of these conditions are preferably simultaneously observed. Good results are observed, furthermore, when either or both of these molar ratios are higher than the preferred respective values, also indicated above, namely:

(i) $H^+/Pd > 200$
(ii) coordinate/Pd > 100.

No advantage is detected in exceeding the following respective values:

(i) in the case of $H^+/Pd$: 5,000 and preferably: 2,500;
(ii) in the case of coordinate/Pd: 2,000 and preferably: 1,500.

The process is typically carried out at a temperature of at least 90° C. in order to observe an appreciable result and, preferably, this temperature remains below 200° C. to limit the risk of degradation of the final products and the starting materials.

In most cases, a reasonable activity and satisfactory results are obtained when the reaction temperature ranges from 120° to 200° C. Very good results may be obtained in the temperature range of 130° to 180° C. The process is normally carried out at a pressure above atmospheric pressure, it being possible for the pressure to be as high as 500 bars (50,000 kPa).

The pressure preferably ranges from 10 to 150 bars 000 and 15,000 kPa). Good results may be obtained using a pressure of from 30 to 120 bars (3,000 and 12,000 kPa).

Upon completion of the reaction, or after a desired residence time, the final products are recovered using any suitable means. For example, the reaction mixture may be subjected to distillation and/or crystallization.

In order to further illustrate the present invention and the advantages thereof, the following specific examples are given, it being understood that same are intended only as illustrative and in nowise limitative. In said examples, the following conventions are used:

Pd mmol/1: denotes the concentration of palladium.
L/Pd: denotes the molar ratio of the coordinate to palladium.
DC (%): denotes the degree of conversion of the nitroaromatic compound.
CY (%): denotes the number of moles of carbamate formed per 100 moles of nitroaromatic compound converted.

EXAMPLE 1

Control tests (a) and (b)

130 ml of a solution containing the following, unless otherwise indicated, were charged into a 300-ml stainless steel autoclave:

(i) nitrobenzene (1.2 mol/1);
(ii) 1,10-phenanthroline (0.03 mol/1);
(iii) mesitylenecarboxylic acid (0.8 mol/1);
(iv) palladium acetate;
(v) ethanol (q.s. 1 l).

Air was then purged out of the autoclave using carbon monoxide, and a pressure of 120 bars (12,000 kPa) of CO was established. The temperature was then raised to 180° C. under stirring, while the pressure was maintained at the value indicated above. After a period at a temperature indicated by t below, the reaction mixture was cooled and degassed and was then analyzed by gas phase and liquid phase chromatography.

The individual conditions and the results obtained are reported in the Table I below:

TABLE I

| Ref. | Pd mmol/l | L/Pd | $H^+/Pd$ | t min | DC (%) | CY (%) |
|---|---|---|---|---|---|---|
| a | 7.6 | 4 | 10.5 | 45 | 100 | 77 |
| b | 2 | 15 | 40 | 90 | 100 | 68 |
| 1(*) | 0.50 | 1,000 | 2,000 | 30 | 100 | 70 |

(*)in this test, the concentrations of 1,10-phenanthroline and of mesitylenecarboxylic acid were as follows: 0.5 mol/l and 1 mol/l, respectively.

The control test (a) is representative of the prior art when the process is used with a relatively high concentration of palladium.

The control test (b) demonstrated that, with a lower concentration of palladium and under the conditions of the prior art, both a lowering of efficiency (more time was required to obtain the same degree of conversion) and a decrease in the selectivity for the desired product were observed.

Example (1), carried out with a low concentration of palladium, but simultaneously employing high molar ratios L/Pd and $H^+/Pd$ according to the present invention, demonstrated the increase in the activity and the preservation of an appreciable selectivity.

EXAMPLES 2 TO 5

Control Tests (c) and (d)

20 ml of a solution containing the following were charged into a 125-ml capacity tantalum autoclave:

(i) nitrobenzene (1.2 mol/l);
(ii) 1,10-phenanthroline;
(III) trifluoroacetic acid;
(iv) palladium acetate;
(v) methanol (q.s. 1 l).

An operating procedure similar to that described in Example 1 was employed, the temperature being 140° C., the pressure 60 bars (6,000 kPa) and the period at the reaction temperature was 4 hours in each test. The individual conditions and the results obtained are reported in Table II below:

TABLE II

| Ref. | Pd mmol/l | L/Pd | $H^+/Pd$ | DC (%) | CY (%) |
|---|---|---|---|---|---|
| c | 5 | 20 | 150 | 100 | 21 |
| d | 0.5 | 20 | 150 | 58 | 40 |
| 2 | 0.5 | 20 | 750 | 67 | 16 |
| 3 | 0.5 | 200 | 150 | 96 | 68 |
| 4 | 0.5 | 600 | 150 | 100 | 79 |
| 5 | 0.5 | 200 | 750 | 100 | 44 |
| e | 2.5 | 20 | 150 | 100 | 54 |
| 6(*) | 2.5 | 120 | 150 | 100 | 61 |

(*) = 90 min

EXAMPLE 6

Control Test (e)

These two tests, the results of which are also reported in Table II, were carried ut under conditions similar to those described for Examples 2 to 5, except that the temperature was 180° C. in both tests and that the duration of Example 6 did not exceed 90 minutes, since the conversion was complete from that time forwards.

EXAMPLES 7 TO 10

Control Test (f)

20 ml of a solution containing the following were charged into a 125-ml capacity tantalum autoclave:

(i) nitrobenzene (1.2 mol/l);

(ii) 1,10-phenanthroline;
(iii) mesitylenecarboxylic acid;
(iv) palladium acetate (0.5 mmol/l);
(v) methanol (q.s. 1 l).

An operating procedure similar to that described for Examples 1 and 2 above was employed, the temperature being 140° C., the pressure 60 bars (6,000 kPa) and the period at reaction temperature 4 h.

The individual conditions and the results obtained are reported in Table III below:

TABLE III

| Ref. | L/Pd | H+/Pd | DC (%) | CY (%) |
|---|---|---|---|---|
| f | 20 | 150 | 24 | 55 |
| 7 | 100 | 150 | 48 | 67 |
| 8 | 600 | 150 | 100 | 75 |
| 9 | 20 | 300 | 21 | 57 |
| 10 | 20 | 1,200 | 31 | 39 |

EXAMPLES 11 TO 13

Control Tests (g) and (h)

A series of tests was carried out in the tantalum autoclave and using an operating procedure similar to that employed previously, starting with 20 ml of a solution containing:
(i) nitrobenzene (1.2 mol/l);
(ii) 1,10-phenanthroline;
(iii) mesitylenecarboxylic acid;
(iv) palladium in the form of the complex Pd(phen)-(OAc)$_2$ (phen: 1,10-phenanthroline) (1.9 mmol/l);
(v) ethanol (q.s. 1 l).

The temperature was 180° C. and the pressure 120 bars (12,000 kPa).

The individual conditions and the results obtained are reported in Table IV below:

TABLE IV

| Ref. | L/Pd | H+/Pd | t min | DC (%) | CY (%) |
|---|---|---|---|---|---|
| g | 11.5 | 20 | 65 | 99 | 41 |
| 11 | 11.5 | 202.3 | 60 | 96 | 82 |
| h | 15.8 | 40.5 | 75 | 100 | 70 |
| 12 | 15.8 | 202.5 | 60 | 100 | 82 |
| 13 | 15.8 | 405 | 40 | 100 | 85 |

EXAMPLE 14

Example 9 above was repeated, the only modification being the nature of the source of palladium which was the complex Pd(dba)$_3$ (dba: dibenzylideneacetone) and the molar ratio of 1,10-phenanthroline to palladium was now 30.
DC = 27%
CY = 64%

EXAMPLE 15

A test was carried out in the tantalum autoclave and following an operating procedure similar to that described above, on a 20-ml charge consisting of:
(i) 24 mmol of nitrobenzene;
(ii) 0.01 mg-at. of palladium in the form of palladium acetate;
(iii) 10 mmol of 1,10-phenanthroline;
(iv) 2 mmol of trifluoroacetic acid;
(v) (q.s. 20 ml) of methanol.
The conditions were as follows.
Pd = 0.5 mmol/l
L/Pd = 1,000; H+/Pd = 200
Temperature = 180° C.
Pressure = 120 bars (12,000 kPa).
The results obtained after two hours at reaction temperature were as follows:
DC = 100%
CY = 62%

EXAMPLE 16

A test was carried out in the tantalum autoclave and following an operating procedure similar to that described above, on a 20-ml charge consisting of:
(i) 24 mmol of nitrobenzene;
(ii) 0.04 mg-at. of palladium in the form of palladium acetate;
(iii) 1 mmol of 2,2'-dipyridyl;
(iv) 7.5 mmol of mesitylenecarboxylic acid;
(v) (q.s. 20 ml) of methanol.
The conditions were as follows:
Pd = 2.0 mmol/l
L/Pd = 25; H+/Pd = 187
Temperature = 140° C.
Pressure = 60 bars (6,000 kPa).
The results obtained after two hours at reaction temperature were as follows:
DC = 47%
CY = 70%

EXAMPLE 17

A test was carried out in the tantalum autoclave and following an operating procedure similar to that described above, on a 20-ml charge consisting of:
(i) 12 mmol of 2,4-dinitrotoluene;
(ii) 0.04 mg-at. of palladium in the form of palladium acetate;
(iii) 1 mmol of 1,10-phenanthroline;
(iv) 7.5 mmol of mesitylenecarboxylic acid;
(v) methanol (q.s. 20 ml)
The conditions were as follows:
Pd = 2.0 mmol/l
L/Pd = 25; H+/Pd = 187
Temperature = 140° C.
Pressure = 60 bars (6,000 kPa).
The results obtained after 4 h at reaction temperature were as follows:
Dinitrotoluene conversion: 100%
Selectivity for dimethyl tolylenecarbamate 60%

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the preparation of an aromatic carbamate, comprising reacting (a) at least one nitroaromatic compound with (b) carbon monoxide and (c) at least one organic compound bearing at least one hydroxyl group, in the presence of:
   (d) a palladium-based catalyst,
   (e) at least one coordinate of the formula:

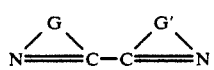

(I)

in which each of G and G', which may be identical or different, is a bridging group which contains 3 or 4 atoms, at least 2 of which are carbon atoms, with the proviso that G and G' may be linked to each other, and (f) at least one protonic acid in which no proton is linked to a halogen atom, and wherein the amount of palladium present in the reaction medium is less than or equal to 0.01 mole per liter of such reaction medium and the reaction is carried out such that:

(i) the molar ratio (H+/Pd) is higher than 150, and (ii) the molar ratio (coordinate/Pd) is higher than 20.

2. The process as defined by claim 1, wherein the molar ratio H+/Pd is lower than 5,000.

3. The process as defined by claim 1, wherein the molar ratio (coordinate/Pd) is lower than 2,000.

4. The process as defined by claim 1, wherein the molar ratio H+/Pd ranges from 200 to 2,500.

5. The process as defined by claim 1, wherein the molar ratio (coordinate/Pd) ranges from 100 to 1,500.

6. The process as defined by claim 1, wherein the concentration of palladium in the reaction medium is lower than 0.0025 mole per liter.

7. The process as defined by claim 1, wherein the at least one coordinate comprises 1,10-phenanthroline.

8. The process as defined by claim 1, wherein the at least one protonic acid comprises mesitylenecarboxylic acid.

9. The process as defined by claim 1, wherein the reaction temperature ranges from 120° to 200° C.

10. The process as defined by claim 1, wherein the reaction pressure ranges from 10 to 150 bars (1,000 to 15,000 kPa).

11. The process as defined by claim 1, said at least one organic compound (c) comprising an alkanol containing not more than 4 carbon atoms.

12. The process as defined by claim 1, said at least one nitroaromatic compound (a) comprising nitrobenzene, a dinitrotoluene, or mixture thereof.

13. The process as defined by claim 9, wherein the reaction temperature ranges from 130° to 180° C.

14. The process as defined by claim 10, wherein the reaction pressure ranges from 30 to 120 bars (3,000 to 12,000 kPa).

15. The process as defined by claim 1, carried out in an inert diluent.

16. The process as defined by claim 1, wherein the at least one protonic acid has a pKa of greater than 2.

* * * * *